(12) United States Patent
Hsu et al.

(10) Patent No.: US 9,051,287 B2
(45) Date of Patent: Jun. 9, 2015

(54) METHOD FOR PRODUCING EPOXIDE

(71) Applicant: China Petrochemical Development Corporation, Taipei (Taiwan), Taipei (TW)

(72) Inventors: Yu-Chuan Hsu, Taipei (TW); Cheng-Fa Hsieh, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 14/065,832

(22) Filed: Oct. 29, 2013

(65) Prior Publication Data

US 2014/0179937 A1 Jun. 26, 2014

(30) Foreign Application Priority Data

Dec. 24, 2012 (TW) .............................. 101149482 A

(51) Int. Cl.
*C07D 301/12* (2006.01)
*C07D 301/03* (2006.01)
(52) U.S. Cl.
CPC .................................... *C07D 301/12* (2013.01)
(58) Field of Classification Search
CPC ............................ C07D 301/12; C07D 301/03
USPC .................................................. 549/531, 523
See application file for complete search history.

(56) References Cited

U.S. PATENT DOCUMENTS

| 5,262,550 | A | * | 11/1993 | Crocco et al. ................. 549/531 |
| 5,290,533 | A | | 3/1994 | Bellussi et al. |
| 5,621,122 | A | * | 4/1997 | Saxton et al. ................. 549/529 |
| 5,684,170 | A | * | 11/1997 | Saxton et al. ................. 549/531 |
| 5,888,471 | A | | 3/1999 | Bellussi et al. |
| 5,977,009 | A | | 11/1999 | Faraj |
| 6,042,807 | A | | 3/2000 | Faraj |
| 6,083,864 | A | | 7/2000 | Bellussi et al. |
| 6,329,537 | B1 | | 12/2001 | Faraj |
| 6,972,337 | B1 | | 12/2005 | Onimus et al. |
| 7,288,237 | B2 | | 10/2007 | Le-Khac |

OTHER PUBLICATIONS

Sandez et al , Impregnation treatments of TS-1 catalysts and their relevance in alkene epoxidation with hydrogen peroxide, 2003, Applied Catalysis A:General 246, p. 69-77.*

* cited by examiner

*Primary Examiner* — T. Victor Oh
(74) *Attorney, Agent, or Firm* — Mintz Levin Cohn Ferris Glovsky and Popeo, P.C.; Peter F. Corless; Richard B. Emmons

(57) ABSTRACT

A method for producing an epoxide is provided. The method includes a step of performing a reaction of an olefine compound and an oxidant to form the epoxide by using a titanium-silicon molecular sieve as a catalyst, thereby increasing the conversion rate of the oxidant and the yield of the epoxide.

12 Claims, 2 Drawing Sheets

METHOD FOR PRODUCING EPOXIDE

CROSS-REFERENCES TO RELATED APPLICATIONS

Figure 1:
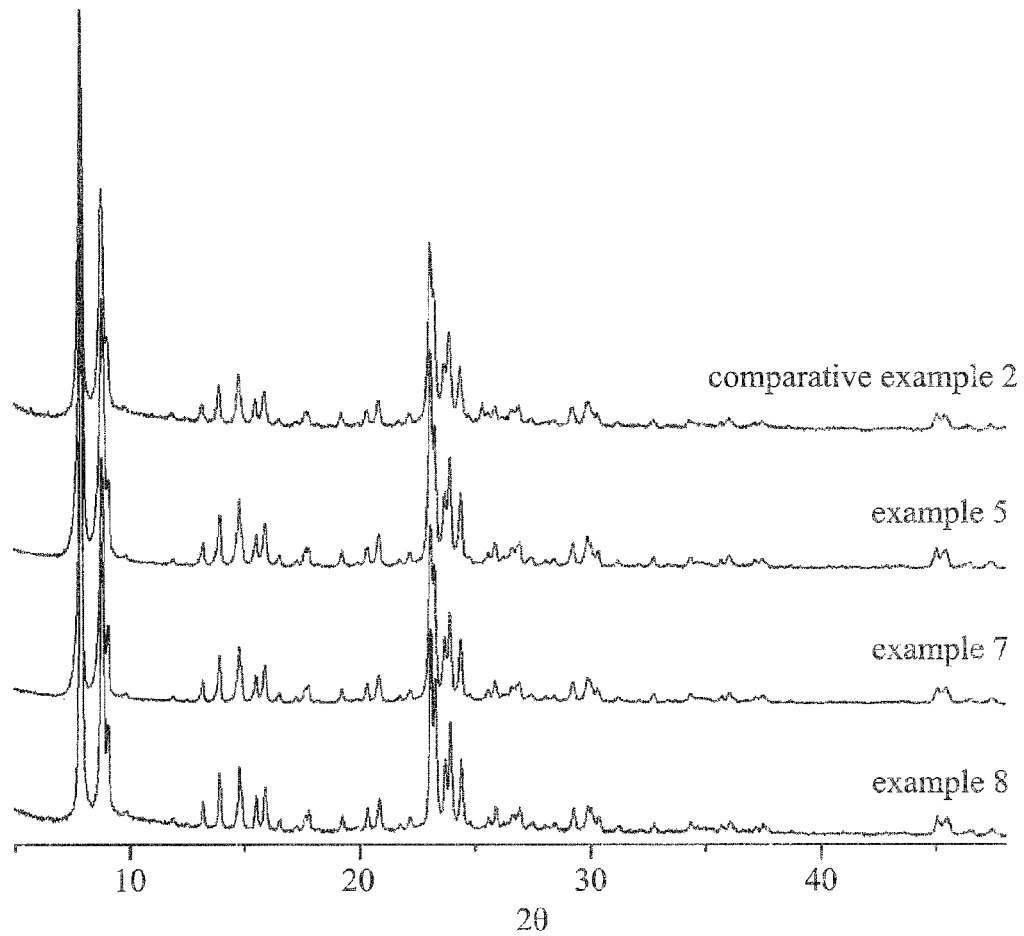

This application claims under 35 U.S.C. §119(a) the benefit of Taiwanese Application No. 101149482, filed Dec. 24, 2012, the entire contents of which is incorporated herein by reference.

FIELD OF THE INVENTION

The present invention relates to methods for producing epoxides, and more particularly, to a method for producing an epoxide using a titanium-silicon molecular sieve containing calcium, strontium or barium as a catalyst.

BACKGROUND OF RELATED ART

Methods for producing epoxides include a chlorohydrin method, a co-oxidation method, a direct oxidation method, and the like. In the chlorohydrin method, a large amount of chlorine-containing sewage, which is detrimental to the environment, is produced after the reaction. The co-oxidation method is complex, and generates various joint products. The direct oxidation method can be classified into an oxygen direct oxidation method and a peroxide direct oxidation method. In the oxygen direct oxidation method for producing an epoxide, pure oxygen is directly introduced as a reactant. The oxygen direct oxidation method is simple, and does not produce any intermediate products. However, the selectivity of the product obtained by the oxygen direct oxidation method is low. In view of the aforesaid drawbacks, the peroxide direct oxidation method using a peroxide as an oxidant to carry out epoxidation is now widely used. In the peroxide direct oxidation method, a titanium-silicon molecular sieve is used as a catalyst which can be easily separated from the product after the reaction. The peroxide direct oxidation method does not harm the environment or consume a large amount of oxygen, but the selectivity and yield of epoxide are yet to be increased.

Usually, a crystalline titanium-silicon molecular sieve is prepared by a hydrothermal method, as mentioned in U.S. Pat. No. 5,290,533, U.S. Pat. No. 5,888,471, U.S. Pat. No. 5,977,009, U.S. Pat. No. 6,042,807, U.S. Pat. No. 6,083,864, U.S. Pat. No. 6,329,537, U.S. Pat. No. 6,972,337 or U.S. Pat. No. 7,288,237, for example. If alkali metal ions or alkaline earth metal ions are present during the preparation of a titanium-silicon molecular sieve in the hydrothermal method, an undesirable crystalline phase is formed. This lowers the catalytic activity of the titanium-silicon molecular sieve. Hence, the presence of these metal ions in the reaction solution should be avoided.

Therefore, it is an urgent issue to develop a method for producing an epoxide with increased raw material conversion rate, product selectivity and yield.

SUMMARY OF THE INVENTION

The present invention provides a method for producing an epoxide, including: performing a reaction of an olefine compound and an oxidant by using a titanium-silicon molecular sieve having a structure of formula (I) as a catalyst in the presence of a solvent to form the epoxide. The titanium-silicon molecular sieve having a structure of formula (I) is as follows:

$$(M_xTi_ySi)O_z \tag{I}$$

wherein M is one selected from the group consisting of Ca, Sr and Ba, X is in a range from 0.0005 to 0.03, y is in a range from 0.005 to 0.06, and z is x+2y+2.

The framework of the titanium-silicon molecular sieve used in the aforesaid reaction is preferably an MFI, MEL, BEA, ZSM-48, MTW or MCM-41 structure. The olefine compound can be any organic compound containing at least one ethylenically unsaturated functional group. The oxidant can be any compounds that generate hydrogen peroxide in the reaction conditions of epoxidation.

The reaction process disclosed in the present invention can be suitably performed in any appropriate reaction vessel or apparatus, such as a fixed bed, transport bed, fluidized bed, stirred slurry, or continuous flow stirred reactor by a batch-type, continuous-type or semi-continuous type approach in a single-phase or two-phase system.

When performing the aforesaid reaction, the amount of catalyst used is not strictly limited, as long as the epoxidation can be completed within the shortest time. In one embodiment, the method of the present invention is performed in batches for epoxidation. Usually, 0.001 to 10 g of a titanium-silicon molecular sieve is used for 1 mole of the olefine compound. In another embodiment, the method of the present invention is performed in a fixed bed reactor. Usually, when epoxidation is performed in a fixed bed reactor, one kilogram of the catalyst quantity per hour is used for 1 to 100 moles of the olefine compound. The titanium concentration in the entire reaction mixture of epoxidation is usually maintained in a range from 10 to 10,000 ppm. The molar ratio of the olefine compound to the oxidant is in a range from 1:100 to 100:1, and preferably in a range from 1:10 to 10:1.

The reaction temperature is not particularly limited, but is in a range from 0 to 150° C., preferably in a range from 25 to 120° C. The reaction is performed for 1 minute to 48 hours, and preferably for 10 minutes to 8 hours. The method of the present invention can be performed at any pressure, but preferably at 1 to 100 atmospheric pressures to increase the solubility of gaseous products.

The method of the present invention is not only simple, but also has advantages like higher epoxide selectivity and higher epoxide yield. Hence, the method of the present invention indeed facilitates industrial applications.

BRIEF DESCRIPTIONS OF THE DRAWINGS

FIG. 1 shows a PXRD analytic spectrum according the comparative example 2 and embodiments 5, 7 and 8 of the present invention.

Figure 2:
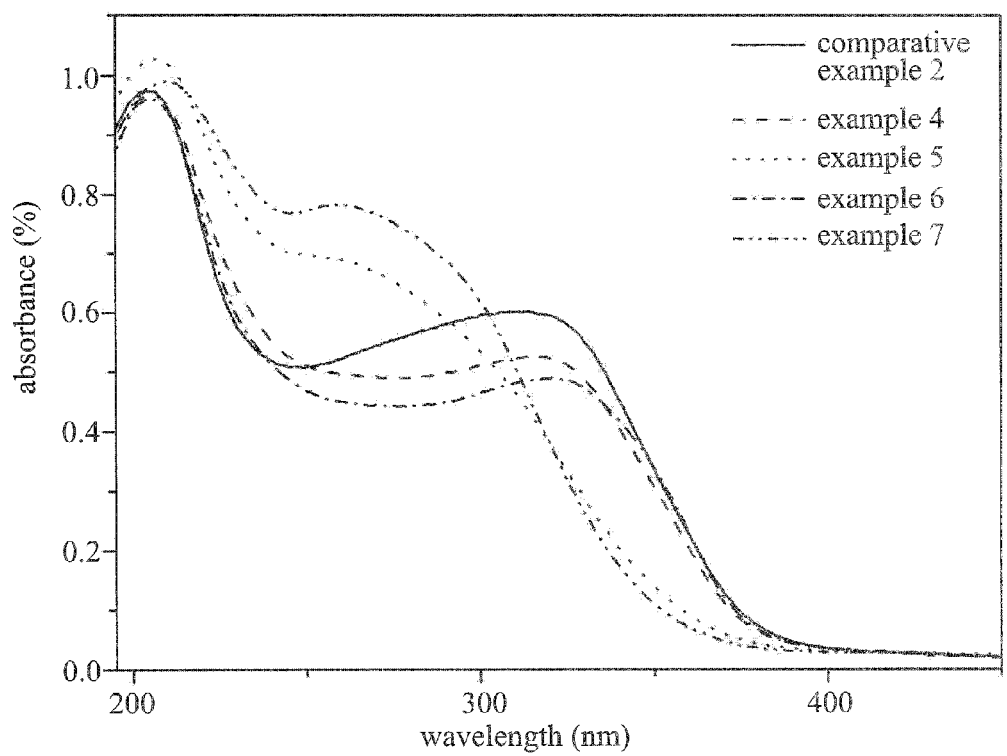

FIG. 2 shows a DR-UV analytic spectrum showing the comparative example 2 and embodiments 4 to 7 of the present invention.

DETAILED DESCRIPTIONS OF THE PREFERRED EMBODIMENTS

In the following, specific embodiments are provided to illustrate the detailed description of the present invention. Those skilled in the art can easily conceive the advantages and effects of the present invention, based on the disclosure of the specification. The present invention can also be further implemented or applied, based on the other different approaches. Each of the details in the specification of the present invention can also be altered or modified without departing from the spirit disclosed in the present invention, in view of the various viewpoints and applications.

The titanium-silicon molecular sieve used in the method of the present invention has a structure of formula (I) in an anhydrous state:

$$(M_xTi_ySi)O_z \qquad (I)$$

wherein M is one selected from the group consisting of Ca, Sr and Ba, x is in a range from 0.0005 to 0.03, y is in a range from 0.005 to 0.06, and z is x+2y+2.

The titanium-silicon molecular sieve may be powdery, bulky, microspherical, monolithic, extrusion molded or in any other forms.

In order to obtain the titanium-silicon molecular sieve, the present invention further provides a method for preparing a titanium-silicon molecular sieve. The method includes the steps of thoroughly mixing a silicon source, a titanium source, a source of an alkaline earth metal and a template, and then heating the mixture to obtain a mixed gel; performing a hydrothermal reaction on the mixed gel at 100 to 200° C. (preferably from 140 to 185° C.) for 1 hour to 10 days (preferably from 6 hours to 3 days); and sintering the mixed gel, which contains the alkaline earth metal and has the hydrothermal reaction performed thereon, at 300 to 800° C. (at an increasing temperature) for 0.5 to 24 hours to obtain a titanium-silicon molecular sieve. Moreover, the method for producing a solid catalyst of the present invention may further include the steps of adding a dispersion into the mixed gel after the mixed gel is formed, and performing a hydrothermal treatment on the mixed gel containing the dispersion, wherein the dispersion is a dispersion including water and a silica sol.

The crystal of the titanium-silicon molecular sieve obtained by the hydrothermal reaction can be isolated from the reaction solution by any suitable conventional method, which includes filtration, centrifugation, decantation or other similar approaches.

The silicon source used in the method for preparing a titanium-silicon molecular sieve of the present invention may be, but not limited to, fumed silicon (silica), silica gel, silica sol, tetraalkyl silicate (such as tetramethyl silicate, tetraethyl silicate, tetrapropyl silicate and tetrabutyl silicate). Examples of silica sol includes Ludox AS-40, Ludox AS-30, Ludox AM-30, Ludox TM-40, Ludox TM-50, Ludox AM-30, Ludox HS-30 and Ludox HS-40 manufactured by DuPont, or SNOWTEX-40, SNOWTEX-50, SNOWTEX-C, SNOWTEX-N, SNOWTEX-20L, SNOWTEX-ZL and SNOWTEX-UP manufactured by Nissan Chemical, or other similar products.

The titanium source used in the method for producing a titanium-silicon molecular sieve of the present invention may be, but not limited to, a titanium salt (such as titanium halide), and tetraalkyl titanate. The titanium sources used in preferred embodiments may be, but not limited to at least one selected from the group consisting of tetramethyl titanate, tetraethyl titanate, tetrapropyl n-titanate, tetrabutyl n-titanate, tetra-sec-butyl titanate, tetrabutyl isotitanate, tetra-t-butyl titanate or a combination thereof.

The source of an alkaline earth metal used in the method for producing a titanium-silicon molecular sieve of the present invention is a calcium source, a strontium source or a barium source, for example, calcium, strontium or barium alkoxides, halides (containing calcium, strontium or barium), hydroxide, carbonate, phosphate, sulphate, nitrate, acetate and silicate.

The template used in the method for producing a titanium-silicon molecular sieve of the present invention may be, but not limited to, an aqueous solution or an alcohol solution of a nitrogen-containing organic alkaline substance, wherein the nitrogen-containing organic alkaline substance is at a concentration in a range from 5 to 50 wt %, and preferably from 20 to 40 wt %. In a preferred embodiment, the nitrogen-containing organic alkaline substance used in the method for producing a titanium-silicon molecular sieve of the present invention may be, but not limited to, alkylammonium hydroxide, such as an aqueous solution or alcohol solution of tetra-n-propylammonium hydroxide; tetra-n-butylammonium hydroxide; alkylammonium halide such as tetra-n-propylammonium bromide, tetra-n-butylammonium bromide; or an organic amine such as triethylamine and ethyldiamine. "Alcohol" in the alcohol solution refers to an alcohol having 1 to 5 carbon atoms, such as methanol, ethanol, isopropanol, n-butanol and t-butanol. The solvent can accelerate the formation of crystals of a titanium-silicon molecular sieve.

In the method for forming a titanium-silicon molecular sieve of the present invention, a molar ration of the nitrogen-containing organic alkaline substance to silicon in the mixed gel are is in a range from 0.1 to 5, preferably from 0.15 to 0.45, and most preferably from 0.2 to 0.4.

The structure of the nitrogen-containing organic alkaline substance can be altered to control the configuration of the titanium-silicon molecular sieve. For example, MFI(ZSM-5), MEL(ZSM-11), BEA(beta), ZSM-48, MTW(ZSM-12) and MCM-41 or other predetermined configurations may be generated. For example, tetrapropylammonium hydroxide is used for generating a titanium-silicon molecular sieve with an MFI configuration.

In the synthetic method described in the present invention, the presence of any alkaline earth metal source can increase the titanium content incorporated into the framework of the molecular sieve. Generally, it is not easy to increase the titanium content incorporated into the framework of the molecular sieve (referring to Millini et al., *J. Catalysis* 137, 497-503 (1992); Millini et al., *Gazzetta Chemica Italiana* 126, 133-140 (1996)). However, the type of the silicon or titanium source reagents used during the hydrothermal process for preparing a TS-1 is altered, so as to make the hydrolytic rates of the reagents more consistent, and thereby to further increase the amount of titanium to be incorporated into the framework (Thangaraj et al., *J. Catalysis* 130, 1(1991); Tuel et al., *Appl. Catal.* 110, 137 (1994)). Further, the molecular sieve as a catalyst is used to catalyze the epoxidation of an alkene so as to provide higher selectivity of epoxides (referring to U.S. Pat. No. 5,262,550). The titanium-silicon molecular sieve containing an alkaline earth metal is prepared by the synthetic method described in the method of the present invention. The titanium content in the framework of the molecular sieve is higher than that of a typical titanium-silicon molecular sieve, confirmed by a DR-UV spectral analysis. The content of the titanium atom content of anatase crystals outside the framework is lower than that of a typical titanium-silicon molecular sieve.

Furthermore, in the titanium-silicon molecular sieve of the present invention, other transitional metals or different atoms may be optionally further incorporated by an immersion method, a precipitation method, a blending method or the like. In the immersion method, a solution of transitional metals is dispersed into an appropriate solvent, then mixed with a molecular sieve to form a titanium-silicon molecular sieve impregnated with the transitional metals. Optionally, the titanium-silicon molecular sieve impregnated with the solution of transitional metals is further dried and sintered, wherein the transitional metals are at concentrations in a range from 0.01 to 10 wt %, and preferably from 0.05 to 5 wt %, based on the total weight of the titanium-silicon molecular sieve of the present invention. Regarding the titanium-silicon molecular sieve impregnated with the solution of transitional metals as prepared by the immersion method, the transitional metals are located in or outside the framework of the titanium-silicon molecular sieve. When the titanium-silicon molecular sieve impregnated with the solution of transitional metals is used as a catalyst in epoxidation, all or some of the transitional metals undergo reduction.

The olefine compound used in the method for preparing an epoxide of the present invention may be, but not limited to, any organic compound containing at least one ethylenically unsaturated functional group (e.g., C═C). The configuration of the organic compound can be annular, dendritic or linear. The organic compound can include aryl group.

In one embodiment, the olefine compounds used in the method for preparing an epoxide may be, but not limited to, $C_2$-$C_{10}$ olefine compound.

The olefine compounds used in the method for preparing an epoxide can be mono-olefine compounds. The mono-olefine compounds include, but are not limited to, ethylene, propylene, 1-butene, 2-butene, 1-pentene and cyclohexene. When the olefine compound is a mono-olefine compound, the molar ratio of the mono-olefine compound to the oxidant is in a range from 1:10 to 10:1.

The oxidant used in the method of an embodiment of the present invention is hydrogen peroxide ($H_2O_2$), but it is not limited to additional hydrogen peroxide which is added to the reaction, and it also may be various compounds which are capable of generating or releasing hydrogen peroxide. For example, when the titanium-silicon molecular sieve impregnated with the solution of transitional metals is used as a catalyst, hydrogen peroxide in the method of the present invention can be formed in-situ. For example, hydrogen and oxygen gases are introduced into an epoxidation reactor containing the titanium-silicon molecular sieve impregnated with the solution of transitional metals (such as palladium and platinum), so as to generate hydrogen peroxide. At this time, no additional feeds of the oxidant are needed.

In the method of the present invention for preparing an epoxide, an additional solvent may be optionally further added to dissolve reactants other than the titanium-silicon molecular sieve, and a better temperature control is provided to increase the rate and selectivity of epoxidation, wherein the solvent ranges from 1 to 99 wt % of the mixture in epoxidation, based on the weight of the mixture in epoxidation. Further, the solvent is in a liquid state at the temperature of epoxidation.

In the method of the present invention for preparing an epoxide, the solvent may be, but not limited to, ketones, ethers, aliphatic or aromatic hydrocarbons, halogenated hydrocarbons, $C_1$-$C_5$ alcohols, water or excessive amount of olefine compounds. Further, the presence of water has no obvious negative impacts on epoxidation. For example, an aqueous solution of hydrogen peroxide can be used in the process for preparing an epoxide without decreasing the yield of epoxides.

Moreover, in the method of the present invention, a catalyst can be activated by any known arts to increase the selectivity of epoxide, by the additions of organic silylation reagents; water-soluble alkaline salts; non-alkaline salts (containing neutral salts, acidic salts); organic molecules containing nitrogen atoms; an aqueous solution or a water-solvent mixed solution of organic acids, inorganic acids or carboxylic ammonium salts containing nitrilo salts; an aqueous solution of hydrogen peroxide with a fluoro ion precursor; or an aqueous solution of hydrogen peroxide containing an anionic substance containing fluorine (referring to the U.S. Pat. No. 4,794,198, U.S. Pat. No. 4,824,976, U.S. Pat. No. 4,937,216, U.S. Pat. No. 5,646,314, U.S. Pat. No. 5,675,026, U.S. Pat. No. 6,060,610, U.S. Pat. No. 6,288,004, U.S. Pat. No. 6,300,506, and U.S. Pat. No. 7,148,381, which are cited herein as references in their entireties).

The implementation of the present invention can be further described by the following specific embodiments. Those skilled in the art can conceive the other advantages and effects of the present invention based on the disclosure of the specification of the present invention. The examples of the present invention are illustrated below, but not for limiting the present invention.

Comparative Example 1

A 500 mL round-bottomed flask was sealed with nitrogen in a vacuum system. 60 grams of tetraethyl silicate and 112 g (20 wt %) of tetra-n-propyl ammonium hydroxide isopropanol solution were added to the round-bottomed flask, and continuously stirred at 5° C. After the temperature reached the equilibrant, 3.38 g of tetra-n-butyl titanate was added to the round-bottomed flask, and continuously stirred for 1 hour. Then, 89.6 g of water was added by an isobaric feeding-tube gradually, and stirred for 1 hour to obtain a gel mixture. Alcohol in the gel mixture was then removed at 85° C. for 1.5 hours. At the same time, a dispersion was prepared by dispersing 21.60 g of silica sol solution (40%) in 147 g of water. The dispersion was added to the gel mixture underwent alcohol removal, and further stirred for 1 hour. The gel mixture (underwent alcohol removal and containing the dispersion) was sealed in a stainless steel pressure-resistant tank with Teflon® lining, and subjected to a hydrothermal reaction at 180° C. for 120 hours. The solid and liquid were separated. The solid part was washed with water to reach neutral state, dried at 100° C., and sintered at 550° C. for 8 hours to obtain a titanium-silicon molecular sieve of comparative example 1 (wherein the ratio of x, y and z is shown in Table 1).

Comparative Example 2

The molecular sieve was prepared by the same process as in comparative example 1 except that the amount of tetra-n-butyl titanate added was 6.90 g in comparative example 2. The ratio of x, y and z in the titanium-silicon molecular sieve is shown in Table 1.

The preparations of the molecular sieve $[(M_xTi_ySi)O_z$ (M=Ca, Sr, Ba)] of the present invention.

Embodiment 1

A 500 mL round-bottomed flask was sealed with nitrogen in a vacuum system. 60 g of tetraethyl silicate and 112 g (20 wt %) of a tetra-n-propyl ammonium hydroxide isopropanol solution were added to the round-bottomed flask, and continuously stirred at 5° C. After the temperature reached the equilibrant, 3.38 g of tetra-n-butyl titanate was added to the round-bottomed flask, and continuously stirred for 1 hour. Then, 0.48 g of calcium chloride and 89.6 g of water were thoroughly mixed, gradually added to the round-bottomed flask using an isobaric feeding-tube, and stirred for 1 hour to obtain a gel mixture. Alcohol in the gel mixture was then removed at 85° C. for 1.5 hours.

At the same time, a dispersion was prepared by dispersing 21.60 g of silica sol solution (40%) in 147 g of water. The dispersion was added to the gel mixture underwent alcohol removal, and further stirred for 1 hour. The gel mixture (underwent alcohol removal and containing the dispersion) was sealed in a stainless steel pressure-resistant tank with Teflon® lining, and subjected to a hydrothermal reaction at 180° C. for 120 hours. The solid and liquid were separated. The solid part was washed with water to reach neutral state, dried at 100° C., and sintered at 550° C. for 8 hours to obtain the titanium-silicon molecular sieve of the present invention (wherein the ratio of x, y and z of embodiment 1 is shown in Table 1).

Embodiment 2

The titanium-silicon molecular sieve was prepared by the same process as embodiment 1 except that calcium chloride was replaced with strontium nitrate (0.91 g) in embodiment 2. The ratio of x, y and z in the titanium-silicon molecular sieve is shown in Table 1.

Embodiment 3

The titanium-silicon molecular sieve was prepared by the same process as embodiment 1 except that calcium chloride was replaced with barium chloride (0.53 g) in embodiment 3. The ratio of x, y and z in the titanium-silicon molecular sieve is shown in Table 1.

Embodiment 4

The titanium-silicon molecular sieve was prepared by the same process as embodiment 1 except that the amount of tetra-n-butyl titanate added was 6.90 g, and the amount of calcium chloride added was 0.048 g in embodiment 4. The ratio of x, y and z in the titanium-silicon molecular sieve is shown in Table 1.

Embodiments 5 to 8

The molecular sieves were prepared by the same process as embodiment 4 except that 0.96 g of calcium chloride (embodiment 5), 0.09 g of strontium nitrate (embodiment 6), 1.83 g of strontium nitrate (embodiment 7), and 2.11 g of barium chloride (embodiment 8) were used. The ratios of x, y and z in the titanium-silicon molecular sieves of embodiments 5 to 8 are shown in Table 1.

The results of the PXRD spectral analysis of the silicon-titanium molecular sieves of the present invention prepared in embodiments 5, 7 and 8 and the molecular sieve prepared in comparative example 2 (no extra amount of a metal source added in comparative example 2) are shown in FIG. 1. The molecular sieves of embodiments 5, 7 and 8 and comparative example 1 all possess a MFI structure. The results of a DR-UV spectral analysis of the titanium-silicon molecular sieves of the present invention, as prepared in embodiments 4 to 7, and comparative example 2 (no extra amount of a metal source added in comparative example 2) are shown in FIG. 2. The contents of the titanium atoms in the framework increased with the increasing proportions of the contents of the alkaline earth metals, and were all more than that of comparative example 2 where no extra amount of an alkaline earth metal source was added. Further, the contents of the titanium atom in anatase crystal outside of the framework decreased with the increasing proportions of the contents of the alkaline earth metals, and were all less than that of comparative example 2 where no extra amount of an alkaline earth metal source was added.

TABLE 1

| Molecular sieve | x | y | z | Framework | Molecular sieve | x | y | z | Framework |
|---|---|---|---|---|---|---|---|---|---|
| Comparative example 1 | — | 0.023 | 2.046 | MFI | Comparative example 2 | — | 0.047 | 2.104 | MFI |
| Embodiment 1 | 0.010 | 0.023 | 2.056 | MFI | Embodiment 4 | 0.001 | 0.047 | 2.095 | MFI |
| Embodiment 2 | 0.010 | 0.023 | 2.056 | MFI | Embodiment 5 | 0.020 | 0.047 | 2.114 | MFI |
| Embodiment 3 | 0.005 | 0.023 | 2.051 | MFI | Embodiment 6 | 0.001 | 0.047 | 2.095 | MFI |
| Note: the structure of the molecular sieve was $(M_xTi_ySi)O_z$ | | | | | Embodiment 7 | 0.020 | 0.047 | 2.114 | MFI |
| | | | | | Embodiment 8 | 0.020 | 0.047 | 2.114 | MFI |

Preparations of Epoxides

Embodiments 9 to 12

The titanium-silicon molecular sieves prepared in comparative example 1 and embodiments 1 to 3 were used, respectively, as a catalyst, to catalyze the reaction of propylene and hydrogen peroxide to produce propylene oxide. The steps of the method for preparing the epoxide are as follows.

A titanium-silicon molecular sieve (the amount added in accordance with the amount shown in Table 2) was thoroughly mixed with 500 g of methanol in a 1 L autoclave. Then, a propylene gas was added in a closed condition to create a pressure of 2 kg/cm², and the reaction temperature was maintained at 40° C. Then, 16.23 g of hydrogen peroxide (35 wt %) was added to the reaction system at a feeding rate of 1.0 mL per minute. The pressure was maintained at 2 kg/cm² using the propylene gas. After the feeding of hydrogen peroxide was completed, the reaction fluid was obtained, the conversion rate of hydrogen peroxide was analyzed by iodometry, and the concentration of the product was analyzed by gas chromatography.

The results are shown in Table 2.

TABLE 2

| Propylene epoxidation | Catalyst | Added amount of catalyst (g) | $X_{H2O2}$ (%) | $S_{PO}$ (%) | $Y_{PO}$ (%) |
|---|---|---|---|---|---|
| Embodiment 9 | Comparative example 1 | 4 | 99.3 | 91.7 | 91.1 |

TABLE 2-continued

| Propylene epoxidation | Catalyst | Added amount of catalyst (g) | $X_{H2O2}$ (%) | $S_{PO}$ (%) | $Y_{PO}$ (%) |
|---|---|---|---|---|---|
| Embodiment 10 | Embodiment 1 | 9 | 99.6 | 95.0 | 94.6 |
| Embodiment 11 | Embodiment 2 | 17 | 99.7 | 92.8 | 92.6 |
| Embodiment 12 | Embodiment 3 | 10 | 99.5 | 94.1 | 93.6 |

$X_{H2O2}$: conversion rate of hydrogen peroxide=number of moles of consumed hydrogen peroxide/total number of moles of fed hydrogen peroxide×100%;

$S_{PO}$: selectivity of propylene epoxide=number of moles of generated propylene epoxide/number of moles of consumed hydrogen peroxide×100%; and $Y_{PO}$: yield of propylene epoxide=number of moles of generated propylene epoxide/total number of moles of fed hydrogen peroxide×100%.

As shown in Table 2 and compared with embodiment 9, in embodiments 10 to 12 of the present invention, the incorporation of various alkaline earth metals in the titanium-silicon molecular sieves with low titanium contents all resulted in greater than 99% of conversion rates of hydrogen peroxide, such that the selectivity and yield of propylene epoxide were increased.

Embodiments 13 to 18

The reaction conditions in embodiments 13 to 18 were the same as in embodiment 9 except that the catalysts used were the titanium-silicon molecular sieves (which were added in accordance with the amounts shown in Table 3) prepared in comparative example 2 and embodiments 4 to 8, respectively. The results are shown in Table 3.

TABLE 3

| Propylene epoxidation | Catalyst | Added amount of the catalyst (g) | $X_{H2O2}$ (%) | $S_{PO}$ (%) | $Y_{PO}$ (%) |
|---|---|---|---|---|---|
| Embodiment 13 | Comparative example 2 | 4 | 99.4 | 84.5 | 84.0 |
| Embodiment 14 | Embodiment 4 | 4 | 99.3 | 88.9 | 88.2 |
| Embodiment 15 | Embodiment 5 | 5 | 99.5 | 88.6 | 88.1 |
| Embodiment 16 | Embodiment 6 | 4 | 99.4 | 86.5 | 86.0 |
| Embodiment 17 | Embodiment 7 | 8 | 99.5 | 91.0 | 90.0 |
| Embodiment 18 | Embodiment 8 | 10 | 99.6 | 93.7 | 93.3 |

As shown in Table 3 and compared with embodiment 13, in embodiments 14 to 18 of the present invention, the incorporation of various contents of alkaline earth metals in the titanium-silicon molecular sieves with high titanium contents all resulted in greater than 99% of conversion rates of hydrogen peroxide, such that the selectivity and yield of propylene epoxide were increased.

It appears from the above embodiments that the method of the present invention not only has simple manufacturing processes, but also has advantages such as higher selectivity of propylene epoxide and high yield of propylene oxide. The method of the present invention indeed has the effect of increasing the production benefit.

The above examples are only used to illustrate the principle of the present invention and the effect thereof, and should not be construed as to limit the present invention. The above examples can all be modified and altered by those skilled in the art, without departing from the spirit and scope of the present invention as defined in the following appended claims.

The invention claimed is:

1. A method for producing an epoxide, comprising:
performing a reaction of an olefine compound and an oxidant in the presence of a solvent to form the epoxide by using a titanium-silicon molecular sieve of formula (I) as a catalyst:

$$(M_xTi_ySi)O_z \qquad (I)$$

wherein M is one selected from the group consisting of Ca, Sr and Ba; x is in a range from 0.0005 to 0.03, y is in a range from 0.005 to 0.06, y increases as x increases, and z is x+2y+2, wherein the catalyst is prepared by preparing a mixture of a silicon source, a titanium source, a source of an alkaline earth metal, a template and water; stirring the mixture to obtain a mixed gel and removing alcohol in the mixed gel; mixing a dispersion with the mixed gel; performing a hydrothermal treatment on the mixed gel containing the dispersion; and sintering the mixed gel.

2. The method of claim 1, wherein the titanium-silicon molecular sieve has a framework selected from the group consisting of MFI, MEL, BEA, ZSM-48, MTW and MCM-41 structures.

3. The method of claim 1, wherein a molar ratio of the olefine compound to the oxidant is in a range from 1:100 to 100:1.

4. The method of claim 1, wherein the olefine compound is a $C_2$-$C_{10}$ olefine compound.

5. The method of claim 4, wherein the olefine compound is a monoolefine compound.

6. The method of claim 5, wherein the monoolefine compound is one selected from the group consisting of ethylene, propylene, 1-butene, 2-butene, 1-pentene and cyclohexene.

7. The method of claim 6, wherein a molar ratio of the monoolefine compound to the oxidant is in a range from 1:10 to 10:1.

8. The method of claim 1, wherein the oxidant is hydrogen peroxide.

9. The method of claim 1, wherein the solvent is one selected from the group consisting of water, $C_1$-$C_5$ alcohols and a combination thereof.

10. The method of claim 1, wherein the solvent is methanol.

11. The method of claim 1, wherein the reaction is performed at a temperature in a range from 0 to 150° C.

12. The method of claim 11, wherein the reaction is performed at a temperature in a range from 25 to 120° C.

* * * * *